United States Patent [19]

Stockum

[11] 4,070,713

[45] Jan. 31, 1978

[54] MEDICAL GLOVE AND METHOD

[75] Inventor: Glenn Francis Stockum, Arlington, Tex.

[73] Assignee: Arbrook, Inc., Arlington, Tex.

[21] Appl. No.: 667,790

[22] Filed: Mar. 17, 1976

[51] Int. Cl.² .......................................... A41D 19/00
[52] U.S. Cl. ........................................................ 2/168
[58] Field of Search .......................... 2/159, 167, 168; 264/131

[56] References Cited

U.S. PATENT DOCUMENTS

| 2,621,333 | 12/1952 | Thomas et al. .......................... 2/168 |
| 2,989,755 | 6/1961 | O'Brien et al. .......................... 2/168 |
| 3,072,914 | 1/1963 | Velonis et al. .......................... 2/167 |
| 3,148,235 | 9/1964 | Velonis et al. ........................ 2/167 X |
| 3,662,054 | 5/1972 | Wollmann et al. .................. 264/131 |
| 3,761,965 | 10/1973 | Barasch .................................... 2/167 |
| 3,813,695 | 6/1974 | Podell et al. ............................ 2/168 |
| 3,872,515 | 3/1975 | Boone et al. ............................ 2/168 |
| 3,942,193 | 3/1976 | Pugh ........................................ 2/167 |

*Primary Examiner*—Werner H. Schroeder
*Attorney, Agent, or Firm*—James R. Hulen

[57] ABSTRACT

A medical glove adapted to tightly conform to a wearer's skin and to be donned without the use of additional lubricants is formed with an outer layer of elastomeric material, an inner layer of elastomeric material bonded to the outer layer and particulate matter securely embedded in and randomly distributed throughout the inner layer. The particulate matter is preferably partially exposed on the inner, skin-contacting surface of the inner layer so that it extends inwardly beyond the surface of the inner layer to provide a lubricating means to facilitate donning of the glove without the use of additional lubricants. A method for making the unique medical glove is also disclosed.

4 Claims, 4 Drawing Figures

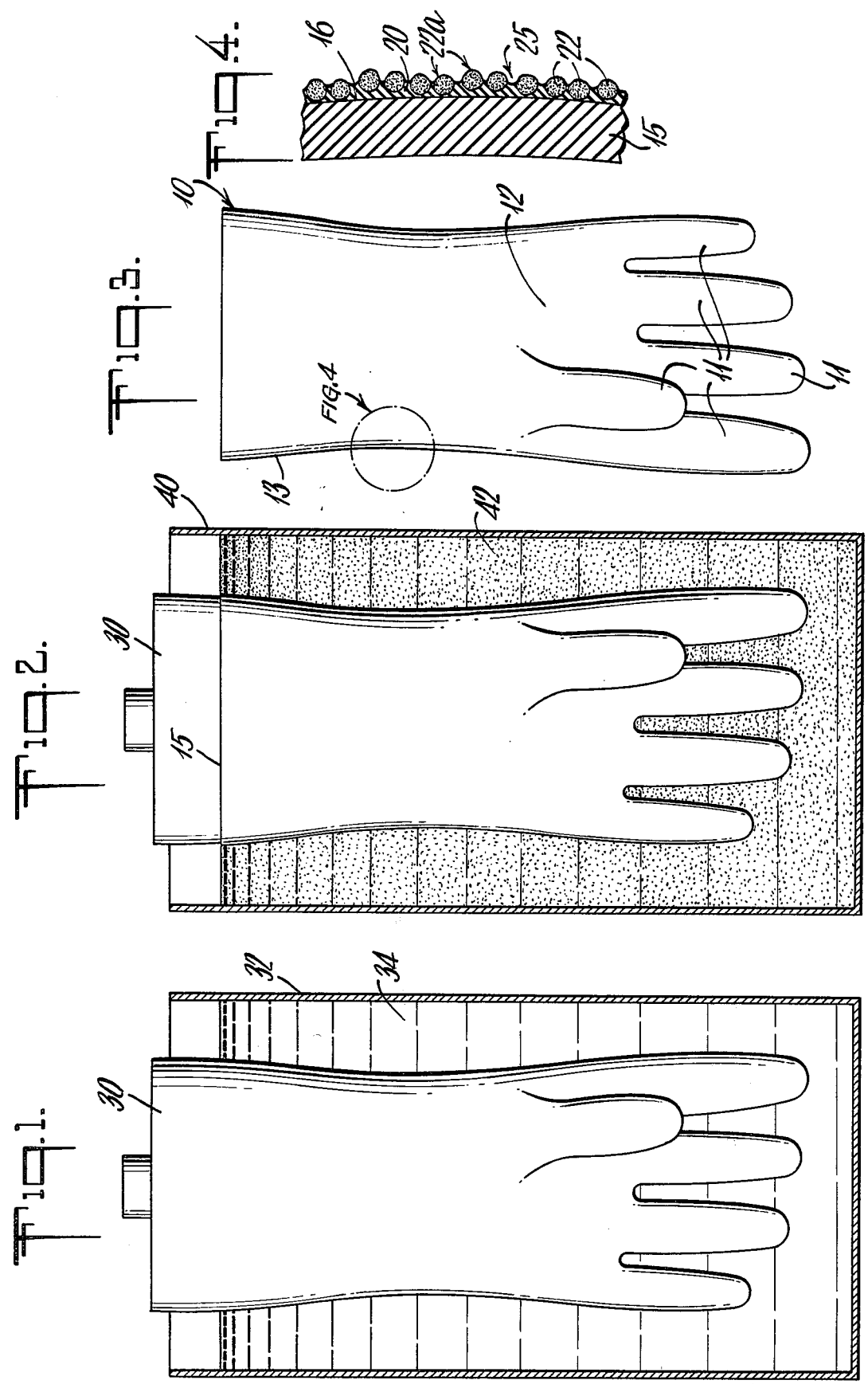

MEDICAL GLOVE AND METHOD

BACKGROUND OF THE INVENTION

This invention relates to medical gloves and, more particularly, it relates to a unique medical glove, and method for making same, that may be easily donned without the use of additional lubricants, such as, the conventional dusting powders.

For medical, surgical and other uses, it is usually necessary that rubber articles of a tightly conforming configuration, such as, gloves, finger cots and the like, be lubricated on the skin-contacting inner surface in order to facilitate donning of the articles. Presently the standard lubricant utilized for this purpose is dusting powder, e.g., cross-linked corn starch. However, certain medical authorities feel that the use of loose dusting powder during surgical procedures may be hazardous in that evidence exists that such dusting powders may cause granuloma and other postoperative complications. Therefore, attempts have been made to eliminate the necessity of using loose dusting powder while at the same time providing an inner glove surface that will aid in the donning of the glove.

Various methods have previously been proposed to provide slip finishes on rubber articles of this type. For example, the surface of a rubber glove can be halogenated with bromine or chlorine to make it slippery. This treatment, however, is very difficult to control in a manufacturing process and the rubber articles are often degraded by these strong oxidants resulting in discolored, hardened articles with a shortened use potential. Furthermore, it has been found that a medical glove surface-treated in this manner is much more difficult to don than an untreated glove dusted with a conventional powder.

It has been further proposed to provide a slip finish comprising a rubber latex blended with a resin latex. This approach also lowers the coefficient of friction of the rubber gloves but they suffer from the same deficit of performance experienced in halogenated gloves in that they cannot be donned without difficulty and certainly not as easily as a powdered glove.

In addition to the foregoing attempts to produce a "powderless glove", it has been proposed to deposit granular material on the inner, skin-contacting surface of a single-layer vinyl or silicone glove in order to reduce the frictional contact between the glove layer and the skin of the wearer and, thus, to aid in the donning of the glove.

Although this approach appears to be promising for a vinyl or silicone glove, the possibility still exists, that the granular material, which is merely deposited on the inner surface of the glove, may be easily abraded from the surface and, thus create problems similar to those experienced with loose dusting powder.

SUMMARY OF THE INVENTION

The present invention is directed to a medical glove which may be easily donned without the use of additional lubricants, such as, loose dusting powder.

This is accomplished in accordance with the present invention by providing a medical glove having an outer layer of elastomeric material, a separate inner layer of elastomeric material bonded to the outer layer and particulate matter securely embedded in and randomly distributed throughout the inner layer. The particulate matter is preferably partially exposed on the inner, skin-contacting surface of the inner layer so that it extends beyond the inner surface to form protrusions on the inner surface in a size and shape, and in a quantity distribution, similar to a powdered glove. The separate inner layer insures that the particulate matter will remain secured to the glove surface and will not be easily abraded therefrom as in the case of prior powderless gloves.

The secure attachment of the particulate matter is further enhanced by the method utilized in making the glove of the present invention. The method is accomplished by initially applying a first layer of elastomeric material, such as natural rubber latex, onto a glove form having the general contour of a human hand. A particulate suspension comprising an elastomeric material having particulate matter randomly distributed therethrough is then provided and applied to the glove form over the first layer. After curing, the first and second layers of elastomeric material are permanently bonded together and the particulate matter is securely embedded within the second layer. Preferably, the particulate matter is greater in size than the thickness of the elastomeric material in the second layer so that the elastomeric material will not entirely cover the surfaces of the particulate matter to thus expose portions of the surfaces on the inner, skin-contacting surface of the glove.

The remaining method steps include stripping of the glove from the glove form and reversing the glove to position the particulate matter on the inner surface thereof.

A glove formed in this manner was found to be easily donned without the use of additional lubricants and the particulate matter remained securely embedded in the inner, skin-contacting layer of the glove.

BRIEF DESCRIPTION OF THE DRAWING

Other objects and attendant advantages of the present invention will become obvious to those skilled in the art from a reading of the following detailed description when read in conjunction with the accompanying drawings wherein:

FIG. 1 is a cross-sectional view of a first dipping tank showing a glove form having a first layer of elastomeric material applied thereto;

FIG. 2 is a cross-sectional view of a second dipping tank showing the glove form of FIG. 1 having a suspension of elastomeric material and particulate matter applied over said first layer of elastomeric material.

FIG. 3 is an elevational view of a finished glove; and

FIG. 4 is a view illustrating an enlarged cross-section of the glove of FIG. 3.

PREFERRED EMBODIMENTS OF THE INVENTION

FIG. 3 illustrates a medical glove 10 constructed in accordance with the present invention. When intended for surgical use, glove 10 is provided with five finger stalls 11, a palm portion 12 and a cuff 13. Obviously, glove 10 may be provided in a variety of sizes by utilizing different sized glove forms during the glove-forming operation.

Referring to FIG. 4, an enlarged cross-sectional view of the wall of glove 10 taken in the area of cuff 13 is illustrated in detail. This cross-sectional view is representative of the uniform thickness and configuration throughout the entire glove body and illustrates the three main components of the glove structure.

Glove 10 is formed with an outer layer 15 of elastomeric material having a desired thickness and flexibility. Outer layer 15 is preferably formed from natural rubber latex because the physical properties and cost of this material have been found to be superior to other elastomeric materials for use in a medical glove.

Securely bonded to the inner surface 16 of outer layer 15 is an inner layer 20 of elastomeric material. Particulate matter 22 is securely embedded in and randomly distributed throughout inner layer 20 and is dimensioned relative to inner layer 20 so that portions 22a thereof are partially exposed on the inner, skin-contacting surface 25 of the glove. In order to accomplish this, the size of particulate matter 22 is greater than the thickness of the elastomeric material in inner layer 20 and, preferably, in the range of 5 to 40 microns. Whereas, the thickness of inner layer 20 is preferably in the range of 5 to 30 microns and the thickness of outer layer 15 is preferably in the range of 125 to 175 microns.

A glove having the above-described construction may be easily donned without the use of additional lubricants, such as loose dusting powder, because the partially exposed particulate matter not only acts as a lubricant between the inner surface of the glove and the skin of the wearer but also forms protrusions which partially isolate inner layer 20 from the skin and thus reduces the overall skin-contacting surface area.

The preferred method for forming the unique medical glove of the present invention is illustrated in FIGS. 1 and 2. Referring first to FIG. 1, a glove form 30 having the general contour of a human hand is shown positioned within a dipping tank 32 which is filled with an appropriate composition 34 of natural rubber latex. Form 30 is preferably of the porcelain type and may be suitably cleaned and treated prior to its immersion in composition 34. The application of outer layer 15 of glove 10 is accomplished in a well known manner by dipping form 30 in composition 34 one or more times to build up layer 15 to the desired thickness.

After layer 15 has been suitably applied to form 30, the form is removed from tank 32 and transferred to tank 40 (see FIG. 2). Suitable mechanical equipment, including form-transfer equipment latex drying equipment and the like may be utilized in the performance of the method of this invention, but has not been described herein in detail because such equipment is considered to be well known to a person having ordinary skill in the art of making natural rubber latex articles.

Tank 40 is filled with a suspension 42 comprising elastomeric material 20 and particulate matter 22. During this dipping operation, suspension 42 becomes deposited on the surface of layer 15 and after a build-up of desired thickness, form 30 is removed from tank 40 and the entire glove assembly is securely bonded together by subsequent treatment in an appropriate curing oven.

Following the curing procedure, glove 10 is stripped from form 30 and reversed so that layer 15, which was adjacent the form, becomes the outer layer of the glove. Preferably, the reversal of the glove is accomplished concurrently with the stripping operation.

Although the exact size and configuration of particulate matter 22 is not critical, certain properties and characteristics of the material have been found to be desirable. The particles should be physiologically inert, smooth in external surface area (preferably spheroidal), low in coefficient of friction and the majority of the particles should be 5 to 40 microns in size. To insure adequate bonding of a given particulate to the elastomeric substrate, specific elastomers are chemically matched to specific particles to resist physical abrasion of the particles from the binder matrix during the donning of the glove.

Representative commercially available particulate matter which is comprised of particles that conform to the size and shape, inertness and lubricity, as outlined, are polyethylene micro beads produced by U.S.I. Corporation under the trade name Microthene and designated by the product codes Microthene FN 500, FN 510, FN 520 and FN 524. Another usable micro bead available from the same supplier is Microthene FN 532, which is an ethylenevinyl acetate copolymer. Many other polymers, naturally occurring as well as man made, are available in the configurations suggested or could be modified to fit the desired parameters.

The presently preferred particulate matter usable with this invention is an epichlorohydrin cross-linked corn starch which is a commercial product of Arbrook, Inc. sold under the trademark BIO-SORB* Absorbable Dusting Powder. The particle size of this material is in the range of 5 to 40 microns.

As stated above, the primary function of the elastomeric material of which inner layer 25 is comprised is to securely bind the low coefficient of friction particulate matter to the inside, skin-contacting surface of highly extensible elastomeric articles, such as natural rubber latex gloves. Therefore the binder must not only provide both static and dynamic adhesion to the particles, but also must possess physical properties, such as tensile strength, elongation, tear strength and modulus comparable to or compatible with the natural rubber substrate.

The binder must also be resistant to the influence of processing chemistry, for example, ethylene oxide or radiation sterilization, and to usage exposures, such as perspiration, scrub soaps and other aqueous exposures relative to the wearing and use of a medical glove or other article. Another pertinent criterion is that the particulate matter/binder composite not contribute to skin sensitization relative to wearing the composite in intimate contact with the skin.

The elastomeric binder which has been found to meet all of the foregoing criteria when utilized in combination with epichlorohydrin cross-linked corn starch is carboxylated styrene butadiene latex.

For a better understanding of the present invention, the following examples illustrate various formulations for the preparation of suspensions to be applied to the inner surface of natural rubber latex gloves to provide a lubricating means to aid in the donning of the gloves.

EXAMPLE I

A glove form having the general contour of a human hand, on which a layer of natural rubber latex is applied to an average thickness of 150 microns, is dipped into a tank containing the following formulation:

|  | Dry wgt. | Wet wgt. |
|---|---|---|
| Carboxylated styrene butadiene latex (low soap) | 100.0 | 200.0 |
| Borated casein solution, 10% solids | 7.5 | 75.0 |
| Zinc oxide dispersion, 50% solids | 5.0 | 10.0 |
| Epichlorohydrin cross-linked corn starch slurry 15% | 20.0 | 133.0 |
| Carboxypolymethylene polymer thickener 500,000 – 1,000,000 molecular weight | .05 | |
| Deionized water - to a solids dilution of 10% | | |

A layer of the formulation is deposited over the layer of natural rubber latex and the form is then removed from the tank. The composite article is then cured and the glove is stripped from the form in a manner that reverses the glove to place the first deposited layer on the outer surface of the glove. The thickness of the inner binder layer is 15 microns and the size of the starch particles is in the range of 5 to 40 microns.

Portions of the starch particles are exposed on the inner, skin-contacting surface of the glove and the glove is easily donned without the use of additional lubricants.

EXAMPLE II

In accordance with the general procedure of EXAMPLE I, a glove is formed utilizing the following formulation:

|  | Parts by wgt. |
|---|---|
| Styrene-polyethylene butylene-styrene block copolymer | 100.0 |
| Pale crepe grade of natural rubber | 10.0 |
| White mineral oil | 100.0 |
| Toluene | 2200.0 |
| Epichlorohydrin cross-linked corn starch | 100.0 |

The glove is found to don easily without the use of additional lubricants.

EXAMPLE III

In accordance with the general procedure of EXAMPLE I, a glove is formed utilizing the following formulation:

|  | Parts by wgt. |
|---|---|
| Brominated butyl rubber | 100.0 |
| Rubber grade stearic acid | 3.5 |
| 2,2'-Methylene bis (4 methyl-6-t-butyl phenol) | 1.25 |
| Parafin wax | 5.0 |
| Mixtron vapor* Talc | 25.0 |
| Petroleum jelly | 2.0 |
| Titanium dioxide, anatase | 2.0 |
| American process zinc oxide | 5.0 |
| Zinc dimethyl dithiocarbamate masticated in a banbury mill or similar rubber compounding device and subsequently dissolved in: | |
| Hexane | 2500 |
| Microthene* FN-510 polyethylene micro beads | 125 |

The glove is found to don easily without the use of additional lubricants.

It will be apparent from the foregoing description that the present invention provides a unique medical glove that may be donned without the use of additional lubricants and that may be easily and economically produced by utilizing conventional glove manufacturing equipment. The method of making the glove contemplates only a single additional step in a standard process for making a natural rubber latex glove, i.e., the application of an inner layer comprising an elastomeric binder and particulate matter.

What is claimed is:

1. A medical glove adapted to tightly conform to the skin of a wearer's hand and to be donned without the use of additional lubricants, comprising: an outer layer of elastomeric material; an inner layer of elastomeric material comprising as a major component thereof carboxylated styrene butadiene latex bonded to said outer layer; and corn starch particles securely embedded in and randomly distributed throughout said inner layer, at least a portion of said particles having a size greater than the thickness of said inner layer and at least a portion of said particles being partially exposed on the inner, skin-contacting surface of said inner layer to form a lubricating means for aiding in the donning of said glove.

2. A medical glove adapted to tightly conform to the skin of a wearer's hand and to be donned without the use of additional lubricants, comprising: an outer layer of elastomeric material; an inner layer of elastomeric material comprising as a major component thereof styrene-polyethylene butylene-stryene block copolymer bonded to said outer layer; and corn starch particles securely embedded in and randomly distributed throughout said inner layer, at least a portion of said particles having a size greater than the thickness of said inner layer and at least a portion of said particles being partially exposed on the inner, skin-contacting surface of said inner layer to form a lubricating means for aiding in the donning of said glove.

3. A medical glove adapted to tightly conform to the skin of a wearer's hand and to be donned without the use of additional lubricants, comprising: an outer layer of elastomeric material; an inner layer of elastomeric material bonded to said outer layer; and polyethylene micro bead particles securely embedded in and randomly distributed throughout said inner layer, at least a portion of said particles having a size greater than the thickness of said inner layer and at least a portion of said particles being partially exposed on the inner, skin-contacting surface of said inner layer to form a lubricating means for aiding in the donning of said glove.

4. The medical glove of claim 3, wherein said inner layer of elastomeric material comprises as a major component thereof brominated butyl rubber.

* * * * *